United States Patent
Ansai et al.

(10) Patent No.: US 8,859,804 B2
(45) Date of Patent: Oct. 14, 2014

(54) METHOD FOR PRODUCING A (METH)ACRYLATE

(75) Inventors: Ryuichi Ansai, Hiroshima (JP); Hiroyuki Nogami, Hiroshima (JP); Kuniyoshi Ogura, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 641 days.

(21) Appl. No.: 13/148,206

(22) PCT Filed: Feb. 4, 2010

(86) PCT No.: PCT/JP2010/051611
§ 371 (c)(1),
(2), (4) Date: Aug. 5, 2011

(87) PCT Pub. No.: WO2010/090258
PCT Pub. Date: Aug. 12, 2010

(65) Prior Publication Data
US 2011/0301379 A1  Dec. 8, 2011

(30) Foreign Application Priority Data
Feb. 5, 2009 (JP) .................. 2009-024835

(51) Int. Cl.
*C07C 67/08* (2006.01)
*C07C 67/54* (2006.01)
*C07C 69/54* (2006.01)

(52) U.S. Cl.
CPC ............. *C07C 67/08* (2013.01); *C07C 67/54* (2013.01)
USPC ............................ 560/220; 560/205; 560/218

(58) Field of Classification Search
CPC .......... C07C 67/08; C07C 67/54; C07C 69/54
USPC ......................... 560/205, 218, 220
See application file for complete search history.

(56) References Cited

U.S. PATENT DOCUMENTS

| 2004/0267045 A1 | 12/2004 | Yada et al. |
| 2011/0137072 A1 | 6/2011 | Ansai et al. |

FOREIGN PATENT DOCUMENTS

| EP | 2 308 820 A1 | 4/2011 | |
| JP | 2000 88018 | 3/2000 | |
| JP | 2000 191590 | 7/2000 | |
| JP | 2000191590 | * 7/2000 | ............. C07C 67/08 |
| JP | 2002 161068 | 6/2002 | |
| JP | 2002 275124 | 9/2002 | |
| JP | 2003 252825 | 9/2003 | |
| WO | WO 2010/016493 A1 | 2/2010 | |

OTHER PUBLICATIONS

International Search Report issued Apr. 6, 2010 in PCT/JP10/51611 filed Feb. 4, 2010.
Extended European Search Report issued Nov. 26, 2012, in European Patent Application No. 10738589.0.

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

Disclosed is a method for producing a (meth)acrylate ester wherein a high purity (meth)acrylate ester is obtained with a high yield, with a reduced loss of (meth)acrylic acid anhydride. In the method, (meth)acrylic acid is recovered with a high yield, and the (meth)acrylate ester is purified easily. Specifically disclosed is a method for producing a (meth)acrylate ester which comprises: (1) a step of producing (meth)acrylic acid anhydride by reacting a specific fatty acid anhydride and (meth)acrylic acid, while removing a by-produced fatty acid; (2) a step of obtaining a (meth)acrylate ester by reacting an alcohol and unpurified (meth)acrylic acid anhydride obtained in step (1) preferably at a temperature not less than 90° C.; and (3) a step of recovering (meth)acrylic acid by distillation preferably at a temperature not less than 90° C. The method may also comprise a step of heating or distilling the reaction liquid obtained in step (2) at a temperature not less than 90° C.

18 Claims, No Drawings

METHOD FOR PRODUCING A (METH)ACRYLATE

TECHNICAL FIELD

The present invention relates to a method for producing and purifying a (meth)acrylate wherein (meth)acrylic acid anhydride obtained by a reaction of (meth)acrylic acid with a fatty acid anhydride is reacted with an alcohol.

BACKGROUND ART

As a method to prepare (meth)acrylate, for example, a method to react (meth)acrylic acid anhydride with an alcohol is known. In patent literature 1, there is described a method to react (meth)acrylic acid anhydride with a secondary or tertiary alcohol under coexistent of a basic compound having 11 or less of acidity (pKa) in water at 25° C. Purified (meth) acrylic acid anhydride is usually used for production of (meth)acrylates using (meth)acrylic acid anhydride. In patent literature 1, there is described purification methods of (meth) acrylic acid anhydride, neutralizing and washing a reaction liquid containing (meth)acrylic acid anhydride with an alkaline aqueous solution of pH7.5 to 13.5, and in patent literature 2, it is described a method of fractional distillation of a crude product.

However, with the method to neutralize and wash a liquid containing (meth)acrylic acid anhydride, it causes a problem that a part of (meth)acrylic acid anhydride is hydrolyzed, and a large quantity of washing-wastewater is generated. As a result, treatment of the wastewater is necessary. With the method to fractionally distill a liquid containing (meth) acrylic acid anhydride, it causes a problem that a part of (meth)acrylic acid anhydride is contained in a initial distilled product or is remained in a reaction vessel and it can be not recovered, and there exists a risk of generation of polymerization during distillation. As mentioned above, with the method to purify (meth)acrylic acid anhydride, the loss of (meth)acrylic acid anhydride can be not avoided.

In patent literature 3, there is described a process for producing phenyl(meth)acrylate characterized in reacting crude (meth)acrylic acid anhydride with a phenol compound. However, according to examinations of the inventors, it was found that compounds, which is obtained by a reaction of acetic acid or (meth)acrylic acid with at least one side of the double bond in (meth)acrylic acid anhydride by the Michael addition reaction, are contained with several percentage in crude (meth) acrylic acid anhydride. When an alcohol is reacted to the compounds obtained by the Michael addition reaction, it is acknowledged generating the compound having a constitution which is obtained by a reaction of (meth)acrylic acid with the (meth)acrylate represented in the following general formula (II) by the Michael addition reaction. Thus, with the preparation method in patent literature 3, it causes a problem that a yield of the (meth)acrylate under the alcohol standard is deteriorated, and, when the (meth)acrylate which is the objective substance is distilled, it causes a problem that the ester represented in general formula (II) is included.

[Formula 1]

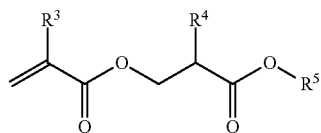

(II)

(In general formula (II), $R^3$ or $R^4$ shows hydrogen or methyl group, and $R^5$ shows an alcohol residue.)

According to examinations of the inventors, it was found that the compound represented in general formula (II) is decomposed into (meth)acrylic acid and a (meth)acrylate at a high temperature. When the (meth)acrylate containing the compound represented in general formula (II) is distilled, (meth)acrylic acid is generated in a late part of distillation at which a distillation liquid temperature becomes high and (meth)acrylic acid is included in the distilled (meth)acrylate, so that purity deteriorates.

When (meth)acrylic acid anhydride and an alcohol are reacted, it may be performed proceeding a method that one of the above component is added with a surplus amount and another component is to be vanished, from the viewpoint of easiness of purification. In addition, when the reaction is not completed, both (meth)acrylic acid anhydride and the alcohol may remain. In particular, when a boiling point of the target product is near to a raw material, namely, when a boiling point of the target product like phenyl methacrylate is near to the boiling point of a feeding alcohol and (meth)acrylic acid anhydride, contents of both raw materials are preferably to be lowered as much as possible.

With the manufacturing method of patent literature 1, (meth)acrylic acid anhydride is dissolved in an alkaline aqueous solution as methacrylic acid transformed by hydrolysis of (meth)acrylic acid anhydride, by using of a surplus amount of (meth)acrylic acid anhydride and by treating of remaining-(meth)acrylic acid anhydride with an alkaline aqueous solution. However, the (meth)acrylate obtained from the alcohol having phenolic hydroxy group is easy to be hydrolyzed, so that the (meth)acrylate is hydrolyzed together when (meth) acrylic acid anhydride is hydrolyzed. As a result, the yield of the (meth)acrylate deteriorates greatly. In addition, (meth) acrylic acid anhydride can be not hydrolyzed efficiently by washing with a weak alkaline aqueous solution such as aqueous solution of sodium carbonate or potassium carbonate. Also, a large quantity of washing-wastewater is generated in these methods.

In patent literature 4, there is described a method to supply a highly reactive alcohol such as methanol and to react the alcohol with remaining-(meth)acrylic acid anhydride. However, an alcohol having methyl ester and phenolic hydroxy group is generated because the (meth)acrylate obtained from an alcohol having phenolic hydroxy group is easy to be transesterificated with methanol. As a result, the yield of the (meth) acrylate deteriorates greatly.

CITATION LIST

Patent Literature

Patent Literature 1: Japanese Patent Laid-Open No. 2002-161,068
Patent Literature 2: Japanese Patent Laid-Open No. 2002-275,124

Patent Literature 3: Japanese Patent Laid-Open No. 2000-191,590

Patent Literature 4: Japanese Patent Laid-Open No. 2002-088,018

SUMMARY OF INVENTION

Technical Problem

The present invention is intended to obtain highly purified (meth)acrylate with the high yield under the condition that loss of (meth)acrylic acid anhydride is restrained, in the case of a method for producing a (meth)acrylate by a reaction of an alcohol with (meth)acrylic acid anhydride, which is obtained by a reaction of (meth)acrylic acid and a fatty acid anhydride. In addition, the present invention is intended to recover (meth)acrylic acid with a high yield by treating a side reaction product. Also, the present invention is intended to facilitate purification of the (meth)acrylate by effectively hydrolyzing the remaining-(meth)acrylic acid anhydride after the reaction.

Solution to Problem

The first invention that can solve the problem is a method for producing a (meth)acrylate comprising the following processes (1), (2), and (3), wherein the reaction in process (2) is carried out at a temperature of 90° C. or more:

(1) a process of producing (meth)acrylic acid anhydride, comprising reacting the fatty acid anhydride represented by the following general formula (I) with (meth)acrylic acid to produce (meth)acrylic acid anhydride, while extracting a fatty acid produced as a by-product;

[Formula 2]

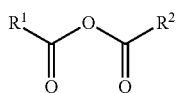
(I)

(In general formula (I), $R^1$ shows a linear or branched, alkyl group or alkenyl group, having carbon number 1 to 3 and $R^2$ shows a linear or branched alkyl group having carbon number 1 to 3.)

(2) a process of obtaining a (meth)acrylate by reacting an alcohol with crude (meth)acrylic acid anhydride obtained by process (1); and (3) a process of recovering (meth)acrylic acid by distillation.

The second invention is a method for producing the (meth)acrylate comprising the above processes (1) to (3), wherein the distillation in process (3) is carried out at 90° C. or more.

The third invention is a method for producing the (meth)acrylate comprising the above processes (1) to (3), wherein process (2'), which is a process that a reaction liquid obtained by process (2) is heated at 90° C. or more, is additionally contained.

The fourth invention is a method for producing the (meth)acrylate comprising the above processes (1) to (3), wherein process (2"), which is a process that the reaction liquid obtained by process (2) is distilled at 90° C. or more, is additionally contained.

The fifth invention is a method for producing the (meth)acrylate comprising the following process (i) and process (ii):

(i) a process of obtaining the (meth)acrylate by reacting the alcohol with (meth)acrylic acid anhydride; and (ii) a process of hydrolyzing remaining-(meth)acrylic acid anhydride by addition of at least one kind of a basic compound selected from hydroxides, carbonates, bicarbonates, and oxides, of alkali metals or alkaline earth metals to the reaction liquid containing the (meth)acrylate, obtained by process (i).

Advantageous Effects of Invention

The method for producing the (meth)acrylate of the present invention can restrain a loss of (meth)acrylic acid anhydride because (meth)acrylic acid anhydride can be used without purification. In addition, because the (meth)acrylic acid, which generated by decomposition of the Michael adducts, mixed to the (meth)acrylate is restrained, the (meth)acrylate can be obtained at high grade and high yield. Also, (meth) acrylic acid can be recovered at the high yield. In addition, purification of the (meth)acrylate can be facilitated by an efficient hydrolysis of remaining-(meth)acrylic acid anhydride after the reaction.

DESCRIPTION OF EMBODIMENTS

In the present invention, the term "(meth)acrylic acid" means at least one of acrylic acid and methacrylic acid. The term "(meth)acrylic acid anhydride" means acrylic acid anhydride, methacrylic acid anhydride, or a mixed acid anhydride with acrylic acid and methacrylic acid. In addition, the term "(meth)acrylate" means at least one of acrylate and methacrylate.

The first, the second, the third, and the fourth inventions comprise process (1), process (2) and process (3) as the basic processes. In addition, the first and second inventions are characterized in respective accomplishment of process (2) or process (3) under the particular condition of temperature. Also, the third and the fourth inventions are characterized in further respective accomplishment of process (2') or process (2") after process (2). In addition, the fifth invention comprises process (i) and process (ii) as the basic processes. Each process is described one by one as follows.

[Process (1): Process to Produce (Meth)Acrylic Acid Anhydride, Comprising Reacting a Fatty Acid Anhydride Represented by the Following General Formula (I) with (Meth)Acrylic Acid to Produce (Meth)Acrylic Acid Anhydride, while Extracting a Fatty Acid Produced as a by-Product;]

[Formula 3]

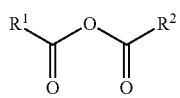
(I)

(In general formula (I), $R^1$ shows a linear or branched, alkyl group or alkenyl group, having carbon number 1 to 3 and $R^2$ shows a linear or branched alkyl group having carbon number 1 to 3.)

In process (1), (meth)acrylic acid anhydride is produced from the fatty acid anhydride and (meth)acrylic acid.

<Fatty Acid Anhydride>

The fatty acid anhydride used as a raw material is a compound represented in general formula (I). In general formula (I), $R^1$ includes methyl group, ethyl group, propyl group, isopropyl group, vinyl group, allyl group, and isopropenyl group. $R^2$ includes methyl group, ethyl group, propyl group, and isopropyl group. For $R^1$, methyl group, ethyl group, and vinyl group are preferable, and methyl group is more preferable from the viewpoint of separation efficiency in a distillation tower of a fatty acid generated as a by-product by the reaction of (meth)acrylic acid and (meth)acrylic acid anhydride obtained. Similarly, for $R^2$, methyl group and ethyl group are preferable, and methyl group is more preferable. From the above reason, acetic anhydride (the acid anhydride between acetic acids) is the most preferable.

When the fatty acid anhydride and (meth)acrylic acid are reacted, (meth)acrylic acid anhydride is produced, and the fatty acid is generated as the by-product. This fatty acid is the same material as the fatty acid which is generated by hydrolysis of the fatty acid anhydride. For example, in the case that the fatty acid anhydride is acetic anhydride, the fatty acid generated as the by-product is acetic acid.

In addition, when (meth)acrylic acid anhydride is produced, a mixed acid anhydride (hereinafter referred to as "the mixed acid anhydride") of the fatty acid coming from the fatty acid anhydride and (meth)acrylic acid may be generated, as an intermediate product. In general formula (I), the mixed acid anhydride is generated in cases except that $R^1$ is a vinyl group derived from acrylic acid for reacting or isopropenyl group derived from methacrylic acid. For example, in the case of the reaction of acetic anhydride with acrylic acid, the mixed acid anhydride having $R^1$ of vinyl group and $R^2$ of methyl group in general formula (I) is generated. Thus, these mixed acid anhydrides can further react with (meth)acrylic acid.

In the present invention, it is preferable that the point when molar ratio of the fatty acid anhydride being the raw material for (meth)acrylic acid anhydride being a product material becomes 0.01 or less be determined as the reaction termination.

However, it is more preferable that the reaction be finished at the condition where quantitative molar ratio of the mixed acid anhydride to (meth)acrylic acid anhydride becomes 0.02 or less because the mixed acid anhydride remains even when quantity of the fatty acid anhydride becomes identification limit or less. For example, when the mixed acid anhydride from acetic acid and (meth)acrylic acid exists in (meth)acrylic acid anhydride, an acetate ester and (meth)acrylic acid are generated at the reaction with the alcohol, so that the yield and selectivity of the target (meth)acrylate deteriorate. It is further preferable that the reaction be finished at the condition when molar ratio of the mixed acid anhydride to (meth)acrylic acid anhydride becomes 0.01 or less, and it is further more preferable that the reaction be finished at the condition when molar ratio of the mixed acid anhydride to (meth)acrylic acid anhydride becomes 0.005 or less, from the viewpoint of the yield of (meth)acrylic acid anhydride, the yield and selectivity of the (meth)acrylate. In addition, protraction of the reaction time leads to increase of the by-product, so that finishing of the reaction at the condition of 0.0001 or more of molar ratio of the mixed acid anhydride to (meth)acrylic acid anhydride is preferable, and finishing of the reaction at the condition of 0.001 or more of molar ratio of the mixed acid anhydride to (meth)acrylic acid anhydride is more preferable.

<(Meth)Acrylic Acid>

In the case of production of (meth)acrylic acid anhydride, it is preferable to use (meth)acrylic acid being a raw material with molar ratio of 1 to 8 times to the fatty acid anhydride. The above molar ratio is preferably 2 or more, and more preferably 2.2 or more, from the viewpoint of the yield of (meth)acrylic acid anhydride based on the fatty acid anhydride. In addition, the above molar ratio is preferably 6 or less, and more preferably 4 or less, from the viewpoint of decrease of recovery load of the quantity of (meth)acrylic acid in the reaction liquid at the reaction termination.

Examples of a method to initially add a raw material into a reactor include:
1) a method to add both all amount of the fatty acid anhydride and all amount of (meth)acrylic acid;
2) a method to add all amount of one of the raw materials into the reactor;
3) a method to add all amount of one of the raw materials and a part amount of the other raw material into the reactor; and
4) a method to add a part amount of both respective ones of the raw materials into the reactor.

In the case of the above methods 2) to 4), the remaining-raw material can be supplied by a method of either divisional addition or continuous addition after a reaction started.

<Catalyst>

In the process for producing (meth)acrylic acid anhydride in the present invention, use of a catalyst is preferable. An unfavorable side reaction such as decomposition, dimerization, trimerization of (meth)acrylic acid anhydride, or Michael addition of (meth)acrylic acid is generated even without existence of a catalyst. In the case of a reaction without a catalyst, the reaction time is extended, and the above side reaction product increases. Examples of the catalyst include a metallic compound, acid catalyst, base catalyst, and heterogeneous catalyst.

Examples of the metallic compound include metallic oxides; metallic hydroxides; salts such as carbonates, bicarbonates, sulfates, chlorides, nitrates, phosphates, and borates, of inorganic acids; organic salts such as acetates, (meth)acrylic acid salts, and sulfonates; and complex salts such as acetylacetonate and cyclopentadienyl complexes.

Examples of the acid catalyst include inorganic acids such as sulfuric acid, nitric acid, phosphoric acid, boric acid, hydrochloric acid and heteropoly-acids, and organic acids such as meta-sulfonic acid, para-toluenesulfonic acid and camphor sulfonic acid. In addition, examples of the base catalyst include organic bases such as pyridine, 4-(dimethylamino) pyridine, and triethylamine. In the above compounds, inorganic acids and organic acids are preferable, and sulfuric acid and sulfonic acid are more preferable, because of high activity and restraint of by-products.

For the heterogeneous catalyst, there can be used ion exchange resins such as basic ion exchange resins and acidic ion exchange resins; and catalytic compounds that active ingredients are fixed on carriers such as silica, alumina, and titania.

In addition, for the above catalyst, it is preferable that all of required amount of the catalyst dissolve in a reaction system from the viewpoint of operability. The catalyst may be used alone or in combination. Examples of a method to add the catalyst into a reactor include a method to initially add all of the catalyst into a reactor, and a method that a part of the catalyst is initially added and the remainder is added later. The amount of the catalyst is preferably 0.000001 to 0.5 times in molar ratio to a charged amount of the fatty acid anhydride represented in the general formula (I) used through the whole reaction. From the viewpoint of proceeding of the reaction smoothly, this molar ratio is preferably 0.000005 times or more, and more preferably 0.00001 times or more. On the other hand, this molar ratio is preferably 0.1 times or less, and more preferably 0.05 times or less, from the viewpoint of removal of the catalyst and restraint of a side reaction.

<Reaction Condition>

The reaction is preferably carried out with absence of a solvent from the viewpoints such as productivity and load of solvent recovering, however, an inert solvent for the reaction can be used if necessary. For the inert solvent, for example, there can be used aliphatic hydrocarbons such as hexane, heptane, pentane, and cyclohexane; aromatic hydrocarbons such as toluene and xylene; ethers such as diethyl ether and diisoprpyl ether; and ketones such as diethyl ketone and diisopropyl ketone. The solvents easy to azeotropically distill with the fatty acid generated as the by-product are preferable. The amount of solvent is preferably 1 to 30 parts by mass to 1 part by mass of (meth)acrylic acid. The reaction temperature at the preparation of (meth)acrylic acid anhydride is preferably 30 to 120° C. The reaction temperature is preferably 50° C. or more, and more preferably 60° C. or more, from the viewpoint of proceeding the reaction smoothly. On the other hand, the reaction temperature is preferably 100° C. or less, and more preferably 90° C. or less, from the viewpoint of restraint of polymerization or the side reaction.

Examples of the reaction method include a batch system that all of the raw material are added in a single reactor and the reaction is finished; a continuous system that the raw material is added continually in a reactor to be reacted continually; and a circuit system, comprising a reactor and a blending tank, that the raw material is reacted while being circulated between the reactor and the blending tank. The batch system is preferable to remove a compound with a boiling point lower than (meth)acrylic acid anhydride such as the fatty acid generated as the by-product, as much as possible.

<Removal of the Fatty Acid>

The reaction is carried out while the fatty acid generated as the by-product is removed outside. Examples of a method to separate the fatty acid generated as the by-product and the other compounds include a method to distill using a distillation tower (a rectification tower) with multiple columns. For the distillation tower, for example, there can be used packed columns using packing materials having forms such as Raschig rings like stainless-steels, glasses and ceramics, Lessing rings, Dixon packing, Paul rings, saddles and Sulzar packing; and plate columns such as perforated plate columns and bubble cap columns. Examples of the connection system with the distillation tower and the reactor include a system that the distillation tower is connected at the top part of the reactor; a system that the distillation tower is connected at the top part of another vessel being connected to the reactor; and a system that the distillation tower is connected to either location between an upper berth and a lower berth of the distillation tower. In all of the above connection systems, there may have one path or plural paths between the reactor and the distillation tower, and apparatus such as exchangers may interpose on the way.

The numbers of theoretical plates of the distillation tower are preferably 3 steps or more, and more preferably 5 steps or more, from the viewpoint of separation efficiency of the fatty acid generated as the by-product with other compounds. On the other hand, 30 steps or less are preferred and 20 steps or less are more preferred, from the viewpoint of a differential pressure and an equipment size.

For the distillation, there can be used an internal reflux system without using a reflux device and a system with controlling a reflux ratio using a reflux device. The reflux ratio can be decided appropriately in consideration of factors such as dimension of an apparatus, productivity and separation efficiency, however, a range of 0.2 to 10 is preferred. The reflux ratio is more preferably 0.5 or more, and further more preferably 1 or more, from the viewpoint of the separation efficiency. On the other hand, 6 or less are more preferred, and 4 or less are further more preferred, from the viewpoint of the productivity. It is preferable that the reflux ratio be adjusted appropriately during the reaction according to the composition of the reaction liquid. In the case of removing the fatty acid generated as the by-product to an outside the system, it is not necessary to completely separate the fatty acid from other compounds. In addition, when the fatty acid anhydride, the mixed acid anhydride, and (meth)acrylic acid anhydride are distilled from the distillation tower with the fatty acid, a part or all of this distillate may be used for another production of (meth)acrylic acid anhydride.

The pressure can be decided appropriately in consideration of the reaction temperature or numbers of steps of the distillation tower. It is preferred to lower the pressure so as to get a condition for carrying out rectification to remove the fatty acid generated as the by-product because a composition of the reaction liquid changes together with progress of the reaction, and an entire steam-pressure deteriorates. The reaction is carried out while the pressure in the distillation tower is regulated, however, the pressure of the top of the tower may be adjusted in consideration of factors such as a reaction temperature and numbers of steps of the distillation tower. Examples of such the method include a method to lower the pressure slowly to the reduced pressure after initiation of the reaction at 80° C. and with an atmospheric pressure.

<Reaction Time>

The reaction time in the reaction can be appropriately determined based on the fatty acid anhydride represented in general formula (I) in the reactor or residual quantity of the mixed acid anhydride. However, the reaction time is preferably 12 hours or more because sizes of the facilities such as the rectification tower become too big in comparison with a manufacturing amount of (meth)acrylic acid anhydride. The reaction time is preferably 15 hours or more, and more preferably 18 hours or more, from the viewpoint of the yield of (meth)acrylic acid anhydride and the size of rectification tower. On the other hand, the reaction time is preferably 72 hours or less, more preferably 60 hours or less, and further more preferably 48 hours or less, from the viewpoint of the productivity. In addition, when the reaction time is shorter, the side reaction is more restrained.

It is noted that the reaction time is defined as the time till the reaction termination from the starting point of the reaction, which is the point of initiation of the removal of the fatty acid in a batch or semibatch reactor. The termination of the reaction is carried out by the stop of removal of the fatty acid or remaining-(meth)acrylic acid.

<Reaction Termination>

According to the present invention, the reaction termination is preferably carried out with a condition in the range of 0.3 to 2 of molar ratio of (meth)acrylic acid to (meth)acrylic acid anhydride in the reaction liquid at the reaction termination. The above molar ratio is preferably 0.5 or more because stability of (meth)acrylic acid improves by making the molar ratio of being more than 0.3, and stability of (meth)acrylic acid anhydride more improves when this molar ratio is bigger. On the other hand, the above molar ratio is preferably 2 or less because of reasons such that a reactor becomes bigger when the amount of (meth)acrylic acid is more in comparison with (meth)acrylic acid anhydride at the case of production of the (meth)acrylate by using of the reaction liquid obtained, and that, as mentioned later, a big volumetric vessel is necessary in storage and load of separation of the (meth)acrylate obtained with (meth)acrylic acid is increased. The above molar ratio is more preferably 1 or less, and further more preferably 0.8 or less. It is noted that, in the present invention, it is preferable to maintain molar ratio of (meth)acrylic acid to (meth)acrylic acid anhydride 0.3 or more through the whole reaction.

<Polymerization Inhibitor>

In the present invention, a polymerization inhibitor can be used for the production of (meth)acrylic acid anhydride. The polymerization inhibitor is introduced in the reactor, and it is preferred being also introduced into the top of the column and the middle of the column, of the distillation tower.

For the polymerization inhibitor, the one inert to acid anhydrides and (meth)acrylic acid is preferred. Examples of the polymerization inhibitor include quinone polymerization inhibitors such as hydroquinone, hydroquinone monomethyl ether, and benzoquinone; alkyl phenolic polymerization inhibitors such as 2,6-di-tert-butylphenol, 2,4-di-tert-butylphenol, 2-tert-butyl-4,6-dimethylphenol, 2,6-di-tert-butyl-4-methylphenol, and 2,4,6-tri-tert-butylphenol; amine-type polymerization inhibitors such as alkylated diphenylamine, N,N'-diphenyl-p-phenylenediamine, and phenothiazine; hindered amine-type polymerization inhibitors such as 4-hydroxy-2,2,6,6-tetramethylpiperidine-N-oxyl, 4-benzoyl oxy-2,2,6,6-tetramethylpiperidine-N-oxyl, and 4-aceto amino-2,2,6,6-tetramethylpiperidine-N-oxyl; metallic copper; copper sulfate; and copper dithiocarbamate-type polymerization inhibitors such as copper dimethyldithiocarbamate, copper diethyldithiocarbamate, and copper dibutyl dithiocarbamate. These polymerization inhibitors may be used alone or in combination.

The amount of the polymerization inhibitor is influenced by a kind of the polymerization inhibitor and a producing condition, however, a range of 0.01 to 10,000 ppm is preferred to the mass of the reaction liquid. In addition, a polymerization prevention effect may be improved by bubbling of gas including oxygen into the reaction liquid.

[Process (2): Process to Obtain the (Meth)Acrylate by the Reaction of the Alcohol with Crude (Meth)Acrylic Acid Anhydride Obtained by the Reaction of Process (1)]

In process (2), the (meth)acrylate is obtained by the reaction of crude (meth)acrylic acid anhydride produced by the above method, with the alcohol.

<Alcohol>

Examples of the alcohol being the raw material include linear or branched aliphatic alcohols such as methyl alcohol, ethyl alcohol, n-propyl alcohol, isopropyl alcohol, n-butyl alcohol, sec-butyl alcohol, tert-butyl alcohol, isobutyl alcohol, n-amyl alcohol, isoamyl alcohol, n-heptyl alcohol, n-octyl alcohol, n-nonyl alcohol, n-decyl alcohol, lauryl alcohol, cetyl alcohol, and stearyl alcohol; unsaturated alcohols such as allyl alcohol and butynediol; cyclic alcohols such as cyclopentanol, cyclohexanol, 1-adamantanol, 2-adamantanol, and 1-adamantane methanol; aromatic alcohols such as phenol and benzyl alcohol; polyols such as ethylene glycol, 1,2-propanediol, 1,3-propanediol, 1,2-butanediol, 1,3-butanediol, 1,4-butanediol, polyethylene glycol, polypropylene glycol, polytetramethylene glycol, and glycerine; alcohols that at least one of hydroxy groups of the polyol is substituted by a substituent such as amino group, carboxyl group, carbonyl group, or amide group; and alcohols having linkages such as ether linkage and ester linkage in a conformation. In these alcohols, alcohols with carbon number 5 or more are preferable from the viewpoint of the separation efficiency the (meth)acrylate generated and (meth)acrylic acid are purified by distillation. In addition, alcohols which do not have a substituent, such as amino group, to react (meth)acrylic acid anhydride are preferable from the viewpoint of selectivity. Even more particularly, alcohols having phenolic hydroxy group are preferable from easiness of decomposition of the Michael adduct.

<(Meth)Acrylic Acid Anhydride>

(Meth)acrylic acid anhydride is preferably used in molar ratio of 0.5 to 5 times to the alcohol when the (meth)acrylate is produced. This molar ratio is more preferably 0.8 or more, and further more preferably 0.9 or more, from the yield of the (meth)acrylate by the alcohol basis. In addition, this molar ratio is more preferably 1.2 or less, and further more preferably 1.1 or less, from the viewpoint of loading-reduction of a treatment or recovery of (meth)acrylic acid anhydride after the reaction The ratio of the alcohol and the (meth)acrylic acid anhydride is appropriately decided from the viewpoints such as easiness of purification after generation of the (meth)acrylate, price of the alcohol, and reactivity of the alcohol.

Examples of a method to initially add a raw material into a reactor include:

1) a method to add both all of (meth)acrylic acid anhydride and all of an alcohol;
2) a method to add all of one or the other of the raw materials into a reactor;
3) a method to add all of one of the raw materials and a part of the other raw material into a reactor; and
4) a method to add a part of one of the raw materials and a part of the other one into a reactor.

In the case of a divisional addition, the remaining-raw material can be supplied by a method of either divisional addition or continuous addition after the reaction started.

<Catalyst>

It is preferable to use a catalyst in the production of the (meth)acrylate. When the catalyst is not used, reaction time is extended, so that polymerization or the side reaction may be generated. For the catalyst, there are used similar catalysts as well as ones used in process (1) such as metallic compounds, acid catalysts, base catalysts, and heterogeneous catalysts.

The catalyst may be used alone or in combination. Examples of a method to add the catalyst include a method to add the total amount initially to a reactor and a method to add a part of one initially and to add the remaining one lately. The catalyst can be used as the same kind of one or the different kind of one in the production of (meth)acrylic acid anhydride. The catalyst used in the production of (meth)acrylic acid anhydride may be kept and used at this stage, or a new one may be added. The amount of the catalyst is preferably 0.0001 to 0.3 times in molar ratio to the alcohol. This molar ratio is more preferably 0.001 or more, and further more preferably 0.01 or more, from the viewpoint of smooth proceeding of the reaction. On the other hand, this molar ratio is preferably 0.2 or less, and more preferably 0.1 or less, from the viewpoint of removal of the catalyst and inhibition of the side reaction.

<Reaction Condition>

It is preferable that the reaction be carried out with absence of the solvent from the viewpoint such as productivity and load of solvent recovering, however, an inert solvent for the reaction can be used if necessary. Examples of such solvent include similar solvents as used in process (1). For the solvent, ones easy to azeotropically distill with (meth)acrylic acid are preferable. The amount of the solvent is preferably 1 to 30 times to the amount of (meth)acrylic acid anhydride.

The reaction temperature is preferably 30 to 150° C. The reaction temperature is more preferably 120° C. or less from the viewpoint of restraint of polymerization or the side reaction. On the other hand, the reaction temperature is more preferably 50° C. or more, and further more preferably 60° C. or more, from the viewpoint of smooth proceeding of the reaction. Generally, in a reaction using a compound which is easy to be polymerized, it is said that reaction at low temperature as possible for prevention of polymerization is preferable. However, it is preferable to proceed the reaction with temperature as high as possible as far as troubles such as the polymerization do not happen because a compound obtained from Michael additional reaction of (meth)acrylic acid with the (meth)acrylate can be easily decomposed in the (meth)acrylate and (meth)acrylic acid by setting of the reaction temperature at 90° C. or more.

For a reaction method, for example, a batch system, continuous system, and circuit system can be adopted as well as the reaction method of (meth)acrylic acid anhydride. The reaction may be carried out during (meth)acrylic acid which is generated as a by-product is recovered. The pressure may be set in the condition of a reduced pressure, atmospheric pressure, or pressurization.

The reaction time producing the (meth)acrylate can be appropriately determined based on residual quantity of (meth)acrylic acid anhydride or the alcohol in the reactor. The reaction is usually finished at the point when molar ratio of at least one of the alcohol and (meth)acrylic acid anhydride to the (meth)acrylate becomes 0.05 or less. This molar ratio is preferably 0.03 or less, and more preferably 0.01 or less, from the viewpoint of reduction of the content of at least one of (meth)acrylic acid anhydride and the alcohol in (meth)acrylic acid recovered. The reaction time may be appropriately decided from the breeding ratio or the reaction temperature, however, it is usually 0.5 to 48 times. The reaction time is preferably 1 hour or more, and more preferably 2 hours or more, from the viewpoint of the yield. The reaction time is preferably 36 hours or less, and more preferably 24 hours or less, from the viewpoint of restraint of polymerization or the side reaction.

<Polymerization Inhibitor>

In the method for producing the (meth)acrylate, a polymerization inhibitor can be used. The polymerization inhibitor is introduced in a reactor, and it is preferred being also introduced into the top of the column and the middle of the column, of the distillation tower. For the polymerization inhibitor, the polymerization inhibitor inert to (meth)acrylic acid anhydride and (meth)acrylic acid is preferable. Examples of the polymerization inhibitor include the polymerization inhibitors as well as ones used in process (1). These polymerization inhibitors may be used alone or in combination. The amount of the polymerization inhibitor is influenced by a kind of the polymerization inhibitor and polymerization condition, however, a range of 0.01 to 10,000 ppm to the mass of the reaction liquid is preferable. In addition, a polymerization prevention effect may be improved by bubbling of gas including oxygen into the reaction liquid.

[Purification of the (Meth)Acrylate]

In the present invention, the highly purified (meth)acrylate can be obtained by purification after vanishing of the alcohol being the raw material from the reaction liquid by adding of excessive amount of (meth)acrylic acid anhydride and treatment of (meth)acrylic acid anhydride in process (2), if necessary. Alternatively, the highly purified (meth)acrylate can be obtained by separation, with methods such as distillation, of the alcohol being the raw material and the (meth)acrylate in the reaction liquid after treatment of (meth)acrylic acid anhydride under the condition when the alcohol being the raw material and (meth)acrylic acid anhydride remain.

<Basic Compound>

The treating method of (meth)acrylic acid anhydride is not limited in particular, however, it is preferable to hydrolyze only remaining-(meth)acrylic acid anhydride by addition of at least one kind of a basic compound selected from hydroxides, carbonates, bicarbonates, or oxides of an alkali metals or an alkaline earth metals into the reaction liquid obtained.

In comparison with alkali metals and alkaline earth metals, hydroxides, carbonates, or bicarbonates of alkali metals are preferable, because solubility of the (meth)acrylic acid salt is low and the (meth)acrylic acid salt may be precipitated. Lithium hydroxide, lithium carbonate, sodium carbonate, and potassium carbonate are preferable from the viewpoint where the possibility in treatment efficiency and hydrolysis of the (meth)acrylate is low. The above compounds may contain water as water of crystallization or the impurity. This treatment may be carried out in concurrence with heating of process (2') mentioned later.

The amount of the basic compound may be 0.1 to 20 moles to 1 mole of (meth)acrylic acid anhydride remained in the reaction liquid. The amount of the basic compound is preferably 0.5 moles or more, and more preferably 1 mole or more, from the viewpoint of treatment efficiency of (meth)acrylic acid anhydride. The amount of the basic compound is preferably 15 moles or less, and more preferably 10 moles or less, from the viewpoint of reduction of a residue of the basic compound. It is necessary to add a quantitative basic compound for neutralizing an acidic compound when the acidic compound is used as the catalyst in process (1) and (2).

<Water>

In the case of this treatment, treatment efficiency of (meth)acrylic acid anhydride is more improved by addition of 0.1 to 10 moles of water to 1 mole of (meth)acrylic acid anhydride remained in the above reaction liquid. The amount of water is preferably 0.3 moles or more, and more preferably 0.5 moles or more, from the viewpoint of treatment efficiency. The amount of water is preferably 5 moles or less, and more preferably 3 moles or less, from the viewpoint of easy purification.

Examples of a method to add the basic compound to a reactor include:
1) a method to add as powder or particles;
2) a method to add as a slurry with water, (meth)acrylic acid or an organic solvent;
3) a method to supply water after adding the basic compound as powder or particles; and
4) a method to add the basic compound as powder or particles after supplying water.

Both divisional addition and continuous addition may be applied.

<Condition of Treatment>

The treatment is preferably carried out with absence of the solvent from viewpoints such as load of productivity and solvent recovering, however, the inert solvent for the reaction can be used if necessary. For the inert solvent, solvents as well as ones used in process (1) can be used. When the inert solvent is used, the amount is preferably 1 to 30 times to a mass of the (meth)acrylate. For the solvent, ones easy to azeotropically distill with the fatty acid generated as the by-product is preferable.

The treatment temperature is preferably a range of 30 to 150° C. The treatment temperature is more preferably 50° C. or more, and further more preferably 60° C. or more, from promotion of a smooth reaction. On the other hand, the treatment temperature is more preferably 140° C. or less, and further more preferably 130° C. or less, from the viewpoint of restraint of polymerization or the side reaction.

Examples of a treatment system include a batch system, continuous system, and circuit system. The treatment time can be appropriately determined from quantity of (meth)acrylic acid anhydride, a charged amount, or the reaction temperature, however, it is usually 0.5 to 48 hours. Reaction time is preferably 1 hour or more, and more preferably 2 hours or more, from the viewpoint of reduction of residual quantity of (meth)acrylic acid anhydride. The reaction time is preferably 36 hours or less, more preferably 24 hours or less, and further more preferably 12 hours or less, from the viewpoint of restraint of polymerization or the side reaction. In the treatment, a polymerization inhibitor can be used. A kind of a polymerization inhibitor and a using method of it can be applied as well as the kind and the using method in process (1).

[Process (3): Process to Recover (Meth)Acrylic Acid by Distillation]

When (meth)acrylate is produced by the reaction of (meth)acrylic acid anhydride with the alcohol in the above process, almost same moles of (meth)acrylic acid as the (meth)acrylate is generated.

<Distillation>

Examples of a method to recover (meth)acrylic acid include a method to distill using a distillation tower (a rectification tower) having a simple column or a multiple column. For the distillation tower, for example, there can be used packed columns using packing materials having forms such as Raschig rings like stainless-steels, glasses and ceramics, Lessing rings, Dixon packing, Paul rings, saddle and Sulzar packing; and plate columns such as perforated plate columns and bubble cap columns. Examples of the connection system with the distillation tower and the reactor include a system that the distillation tower is connected at the top part of the reactor; a system that the distillation tower is connected at the top part of another vessel being connected to the reactor; and a system that the distillation tower is connected to either location between an upper berth and a lower berth of the distillation tower. In all of the above connection systems, the reactor and the distillation tower may have one path or plural paths, and apparatus such as exchangers may interpose on the way.

The numbers of theoretical plates of the distillation tower are preferably 3 steps or more, and more preferably 5 steps or more, from the viewpoint of the degree of purity of the recovering-(meth)acrylic acid. On the other hand, 30 steps or less are preferred, and 20 steps or less are more preferred, from a differential pressure and the viewpoint of the equipment size. For the distillation, there can be used an internal reflux system without using a reflux device and a controlling system of a reflux ratio using a reflux device. The reflux ratio can be decided appropriately in consideration of factors such as dimension of the apparatus, productivity, and separation efficiency, however, a range of 0.2 to 10 is preferable. The reflux ratio is more preferably 0.5 or more, and further more preferably 1 or more, from the viewpoint of the degree of purity of (meth)acrylic acid. On the other hand, 6 or less are more preferable, and 4 or less are further more preferable, from the viewpoint of the productivity. It is preferable that the reflux ratio be adjusted appropriately during the reaction according to the composition of the reaction liquid.

The temperature of the reaction liquid in the reactor (hereinafter referred to as "distillation temperature") is applied at approximately 10 to 150° C. The distillation temperature is preferably 140° C. or less, and more preferably 130° C. or less, from the viewpoint of restraint of polymerization or the side reaction. On the other hand, the distillation temperature is preferably 30° C. or more, and more preferably 50° C. or more, from the viewpoint of enough keeping of a steam quantity. When the alcohol and crude (meth)acrylic acid anhydride are reacted at less than 90° C. in the last process, it is preferable that the distillation temperature be set 90° C. or more from the initial stage or the middle stage of distillation. The compound obtained from Michael additional reaction of (meth)acrylic acid with the (meth)acrylate can be easily decomposed in the (meth)acrylate and (meth)acrylic acid by setting of the reaction temperature at 90° C. or more.

The pressure can be decided appropriately in consideration of the distillation temperature or numbers of steps of the distillation tower. Distillation under reduced pressure is preferable from the viewpoint that distillation temperature can be lowered.

<Polymerization Inhibitor>

In the recovery of (meth)acrylic acid, a polymerization inhibitor can be used. It is preferred that the polymerization inhibitor be not only introduced in a reactor, but also introduced into the top of the column and the middle of the column, of the distillation tower. For the polymerization inhibitor used in the reactor, the polymerization inhibitor inert to (meth)acrylic acid anhydrides and (meth)acrylic acid is preferable. Examples of the polymerization inhibitor include the polymerization inhibitors as well as ones used in process (1). These polymerization inhibitors may be used alone or in combination.

The recovered amount of (meth)acrylic acid is preferably 96% by mass or less, more preferably 94% by mass or less, and further more preferably 92% by mass or less of (meth)acrylic acid contained in the reaction liquid for treatment, from the viewpoint of reduction of the contaminant content contained in (meth)acrylic acid recovered.

(Meth)acrylic acid recovered can be used in process (1) or another reaction again. Highly purified (meth)acrylic acid or (meth)acrylic acid with a little contaminant except (meth)acrylic acid anhydride can be used directly for process (1) as fresh (meth)acrylic acid. (Meth)acrylic acid containing contaminants such as (meth)acrylic acid anhydride, the (meth)acrylate and the alcohol can be used for process (2). (Meth)acrylic acid with the contaminant may be distilled again. The distillation may be carried out only for the fraction obtained by this operation, or may be carried out for the mixture with a reaction liquid or a fraction, containing the (meth)acrylate, which was produced newly.

When recovering-(meth)acrylic acid is used, (meth)acrylic acid in which a new extra one was added may be used. When (meth)acrylic acid in which a new extra one was added may be used, the ratio of recovering-(meth)acrylic acid and new (meth)acrylic acid can be 1 to 99 parts by mass of new (meth)acrylic acid to 100 parts by mass of recovering-(meth)acrylic acid. It is noted that the above-mentioned process and the recovering-(meth)acrylic acid may be used once or repeated several times.

In the above explanation, there were described particular conditions such as temperature condition in process (1), process (2) and process (3) which are basic processes of the present inventions, and temperature condition in process (2) and process (3) which are characterized in the first and the second invention.

Successively, there are described the third and the fourth inventions characterized in the proceeding of particular process (2') or process (2") after process (2), respectively.

[Process (2'): Process for Heating the Reaction Liquid Obtained in Process (2) at 90° C. or More]

<Heat Treatment>

The compound obtained from Michael additional reaction of (meth)acrylic acid with the (meth)acrylate can be easily decomposed in the (meth)acrylate and (meth)acrylic acid by heat treatment at 90° C. or more of the reaction liquid containing the (meth)acrylate obtained in the aforementioned method after process (2), if necessary. The heat treatment temperature is preferably 90 to 150° C. The heat treatment temperature is more preferably 100° C. or more, and further more preferably 120° C. or more, from the viewpoint of the time of heat treatment. On the other hand, the heat treatment temperature is more preferably 140° C. or less, and further more preferably 130° C. or less, from the viewpoint of restraint of polymerization or the side reaction.

The heat treatment may be carried out in a condition that the catalyst used in the prior process remains or may be carried out after the catalyst was removed with a treating agent such as an adsorbent. When the acid catalyst or base catalyst exists, neutralization may be applied with a basic compound or an acidic compound. When the acid catalyst exists, neutralization by the basic compound is preferable from the viewpoint of restraint of polymerization or decomposition of (meth)acrylate.

Examples of the basic compound include oxides, hydroxides, carbonates, or bicarbonates of alkali metals or the alkaline earth metals; and organic basic compounds such as carboxylates like acetates or (meth)acrylic acid salts, pyridine, 4-(dimethylamino)pyridine, and triethylamine. Examples of the acidic compound include inorganic acids such as sulfuric acid, nitric acid, phosphoric acid, boric acid, hydrochloric acid and the heteropoly acid, and organic acids such as meta-sulfonic acid, para-toluenesulfonic acid and camphor sulfonic acid.

It is preferable that the heat treatment be carried out with absence of a solvent from the viewpoint of factors such as productivity and load of solvent recovering, however, an inert solvent can be used for the reaction, if necessary. Examples of the inert solvent include similar solvents as used in process (1). The amount of the solvent is preferably 1 to 30 times to the mass of (meth)acrylic acid. For the solvent, ones easy to azeotropically distill with (meth)acrylic acid generated as the by-product are preferable. The pressure may be set in the condition of a reduced pressure, atmospheric pressure, or pressurization.

The heat treatment time may be appropriately decided from quantity of the Michael adduct of (meth)acrylic acid or the heat treatment temperature, however, it is usually 0.5 to 48 hours. Reaction time is preferably 1 hour or more, and more preferably 2 hours or more, from the viewpoint of decomposition amount of the Michael adduct of (meth)acrylic acid. Reaction time is preferably 36 hours or less, more preferably 24 hours or less, and further more preferably 12 hours or less, from the viewpoint of restraint of polymerization or the side reaction.

In the heat treatment, a polymerization inhibitor can be used. For the polymerization inhibitor, the polymerization inhibitor inert to the (meth)acrylate and (meth)acrylic acid is preferable. Examples of the polymerization inhibitor include the polymerization inhibitors as well as ones used in process (1). These polymerization inhibitors may be used alone or in combination. The amount of the polymerization inhibitor is influenced by a kind of the polymerization inhibitor and polymerization condition, however, a range of 0.01 to 10,000 ppm to the mass of the reaction liquid is preferable. In addition, a polymerization prevention effect may be improved by bubbling of gas containing oxygen into the reaction liquid.

[Process (2"): Process of Obtaining the Reaction Liquid Containing (Meth)Acrylic Acid and the (Meth)Acrylate by Distillation of the Reaction Liquid Obtained by Process (2) at 90° C. or More]

The fourth invention is a method for producing a (meth)acrylate carrying out process (2") between process (2) and process (3).

<Distillation>

In the present invention, both of the (meth)acrylate and (meth)acrylic acid can be recovered together by distillation of the reaction liquid containing the (meth)acrylate and (meth)acrylic acid. For the distillation tower, there can be adopted a connection aspect with the distillation tower and the reactor, the number of theoretical plates of the distillation tower, presence of the reflux device, a reflux ratio, a pressure control standard of the distillation tower, selection judgment and an addition point of the polymerization inhibitor, the same conditions as the conditions of process (3).

The distillation temperature can be set in the range of 10 to 200° C. The distillation temperature is preferably 140° C. or less, and more preferably 130° C. or less, from the viewpoint of restraint of polymerization or the side reaction. The distillation temperature is preferably 30° C. or more, and more preferably 50° C. or more, from the viewpoint of maintaining of a enough steam quantity. The compound obtained from Michael additional reaction of (meth)acrylic acid with the (meth)acrylate can be easily decomposed in the (meth)acrylate and (meth)acrylic acid by setting of distillation temperature at 90° C. or more from the beginning or the middle of the distillation.

The recovered mixture of the (meth)acrylate and (meth)acrylic acid can be separately recovered as the (meth)acrylic acid and (meth)acrylate by an additional distillation. The distillation may be carried out only for the fraction obtained by this operation, or may be carried out for the mixture with a reaction liquid or a fraction, containing the (meth)acrylate, which was produced newly. In addition, the (meth)acrylate and (meth)acrylic acid can be recovered in the separate state by an operation such as extraction, washing, or crystallization.

A liquid containing the (meth)acrylate as a main component is obtained by recovering and removing of (meth)acrylic acid with an operation such as distillation from the reaction liquid containing the (meth)acrylate and (meth)acrylic acid obtained in the process for production of the (meth)acrylate.

In the present invention, it is preferable to hydrolyze the only remaining-(meth)acrylic acid anhydride by adding at least one kind of a basic compound selected from hydroxides, carbonates, bicarbonates, and oxides of alkali metals or alkaline earth metals to a distillate containing the (meth)acrylate and (meth)acrylic acid obtained in the aforementioned process (2"), if necessary. The treatment method of (meth)acrylic acid anhydride in this case is the same as the method mentioned in process (2).

[Purification of the (Meth)Acrylate]

In the present invention, a highly purified (meth)acrylate can be obtained by purification after process (3) of (meth)acrylic acid recovered in process (3), if necessary. The purification method is not limited in particular, however, examples of the purification method include distillation, absorptive treatment, washing, and crystallization.

Examples of the method to distill (meth)acrylate include methods such as simple distillation, distillation by a multiple distillation tower (rectification tower), and thin film distillation. There can be applied with the same conditions as the conditions of process (2"), the distillation tower, a connection aspect with the distillation tower and the reactor, the number of theoretical plates of the distillation tower, presence of the reflux device, a reflux ratio, a pressure control standard of the distillation tower, selection judgment and an addition point of the polymerization inhibitor.

<Washing>

Examples of a method to wash the (meth)acrylate include a method to wash by water, an aqueous solution of a salt such as sodium chloride or sodium sulfate, or an aqueous solution of a basic substance. Examples of the basic substance include hydroxides of alkali metals such as sodium hydroxide and potassium hydroxide; hydroxides of alkaline earth metals such as calcium hydroxide and magnesium hydroxide; carbonates of alkali metals such as sodium carbonate and potassium carbonate; carbonates of alkaline earth metals such as calcium carbonate and magnesium carbonate; bicarbonates of alkali metals such as sodium bicarbonates and potassium hydrogen carbonate; bicarbonates of alkaline earth metals such as calcium hydrogencarbonate and magnesium hydrogencarbonate; and organic basic compounds such as pyridine, 4-(dimethylamino)pyridine and triethylamine. These basic compounds are used alone or in combination. Washing may be with one time or with several times. In addition, multiple washing can be applied by using of aqueous solutions of different basic compounds. After washing with a basic compound, it is preferable to wash with water to exclude a basic compound remaining in the organic layer. For water used for washing, distilled water and pure water deionized with an ion exchange resin are preferable.

The density of salts or the basic compound in an aqueous washing solution is preferably 1 to 30% by mass, and more preferably 2 to 15% by mass. When density of the washing water is less than 1% by mass, enough washing effect can be not obtained. On the other hand, when density of the washing water is more than 30% by mass, a precipitate may be generated. When the (meth)acrylate is washed, using of an organic solvent is not necessary, however, it is possible to mix an organic solvent with the reaction liquid containing the (meth) acrylate, if necessary. For the solvent, the same solvent as the one described in process (2) can be used. Mass of the solvent to the reaction liquid is preferably 0.1 to 10 times, and more preferably 0.5 to 5 times. When this mass ratio is less than 0.1 times, it may be generated transferring the (meth)acrylate to water or an aqueous solution, used for washing. On the other hand, when this mass ratio is more than 10 times, it takes much time to recover the solvent.

<Adsorption Treatment>

Examples of the method of adsorption treatment of the (meth)acrylate include a method by column chromatography and a method to separate a adsorbent after an impurity was adsorbed with a suspension of the adsorbent. Examples of the adsorbent include activated soil, hydrotalcites, porous polymers, ion exchange resins (cation exchange resins or anion exchange resins), activated carbon, adsorption resins, silicagel, silica alumina-type adsorbents, alumina gel, activated alumina, silicon dioxide, and zeolite.

The amount of the adsorbent is 0.05 to 20% by mass to the (meth)acrylate. Particularly, the amount of the adsorbent is preferably 0.5 to 10% by mass. When the amount of the adsorbent is too little, a reduction effect of the impurity is not sufficient. When the amount of the adsorbent is too much, total adsorbed amounts of the (meth)acrylate to the adsorbent increase, so that loss of the (meth)acrylate by adsorption or the load at the case of separation of the adsorbent by filtration becomes large.

A temperature when the (meth)acrylate is contacted with the adsorbent is not limited, however, it is usually 0 to 100° C. The contacting temperature is preferably 60° C. or less, and more preferably 40° C. or less, from the viewpoint of restraint of the side reaction at the treatment. The time of contacting of the reaction liquid with the adsorbent is different by the kind or the amount of the adsorbent, however, usually, it is preferably around 1 to 120 minutes, and more preferably around 3 to 60 minutes.

After adsorption treatment by the adsorbent, the (meth) acrylate can be separated from the adsorbent by a method such as filtration, for example. Examples of the filter include a membrane filter made by a fluororesin such as polytetrafluoroethylene is included.

When the (meth)acrylate is contacted with the adsorbent, using of an organic solvent is not necessary, however, it is possible to mix an organic solvent with the reaction liquid containing the (meth)acrylate, if necessary. For the solvent, the same solvent as the one described in process (1) can be used. Mass of the solvent to the reaction liquid is preferably 0.1 to 10 times, and more preferably 0.5 to 5 times. When this mass ratio is less than 0.1 times, transfer of the (meth)acrylate to water or an aqueous solution, used for washing may be generated. On the other hand, when this mass ratio is more than 10 times, it takes much time to recover the solvent.

<Crystallization>

Examples of the method to crystallize the (meth)acrylate include a method to precipitate a crystal by lowering the temperature of the reaction liquid and a method to precipitate a crystal by concentration with excluding a low temperature-boiling compound. When crystallization is carried out, a solvent may be added. For the solvent, saturated hydrocarbons are preferable. Examples of the solvent include hexane, cyclohexane, methylcyclohexane, ethylcyclohexane, heptane, nonane, octane, isooctane, decane, benzene, toluene, xylene, cumene, and ethylbenzene. These may be used alone or in combination. For purification, distillation is the most preferably from the viewpoint of the ratio of recovery of (meth)acrylic acid.

The fifth invention is a method for producing the (meth) acrylate containing the following process (i) and process (ii):
(i) a process of obtaining a (meth)acrylate by reacting an alcohol with (meth)acrylic acid anhydride; and
(ii) a process of hydrolyzing remaining-(meth)acrylic acid anhydride by addition of at least one kind of a basic compound selected from hydroxides, carbonates, bicarbonates, and oxides of alkali metals or alkaline earth metals to the reaction liquid containing the (meth)acrylate, obtained by process (i).

[Process (i)]

The process (i) can be carried out like process (2).

[Process (ii)]

<Basic Compound>

The basic compound is used in process (ii). In comparison with alkali metals and alkaline earth metals, hydroxides, carbonates, or bicarbonates of alkali metals are preferable, because solubility of the (meth)acrylic acid salt is low and the (meth)acrylic acid salt may be precipitated. Lithium hydroxide, lithium carbonate, sodium carbonate, and potassium carbonate are preferable from a point that the possibility in treatment efficiency and hydrolysis of the (meth)acrylate are low. The above compounds may contain water as one of crystallization or the impurity.

The amount of the basic compound may be 0.1 to 20 moles to 1 mole of (meth)acrylic acid anhydride remained in the reaction liquid. The amount of the basic compound is preferably 0.5 moles or more, and more preferably 1 mole or more, from the viewpoint of treatment efficiency of (meth)acrylic acid anhydride. The amount of the basic compound is preferably 15 moles or less, and more preferably 10 moles or less, from the viewpoint of amount of a residue of the basic compound. It is necessary to add a quantitative basic compound for neutralizing an acidic compound when the acidic compound is used as the catalyst in process (i).

<Water>

In the case of this treatment, treatment efficiency of (meth) acrylic acid anhydride is more improved by adding 0.1 to 10 moles of water to 1 mole of (meth)acrylic acid anhydride remained in the above reaction liquid. The amount of water is preferably 0.3 moles or more, and more preferably 0.5 moles or more, from the viewpoint of treatment efficiency. The amount of water is preferably 5 moles or less, and more preferably 3 moles or less, from the viewpoint of easy purification.

Examples of a method to add the basic compound to a reactor include:
1) a method to add the basic compound as powder or particles;
2) a method to add the basic compound as a slurry with water, (meth)acrylic acid or an organic solvent;
3) a method to supply water after adding the basic compound as powder or particles; and
4) a method to add the basic compound as powder or particles after supplying water.

Both of divisional adding and continuous adding may be applied.

<Solvent>

The treatment is preferably carried out with absence of a solvent from the viewpoints such as load of productivity and solvent recovering, however, an inert solvent for the reaction can be used if necessity. For the inert solvent, solvents as well as ones used in process (1) can be used. When the inert solvent is used, the amount is preferably 1 to 30 times to a mass of the (meth)acrylate. For the solvent, ones easy to azeotropically distill with fatty acid generated as the by-product are preferable.

<Reaction Condition>

The treatment temperature is preferably a range of 30 to 150° C. The treatment temperature is more preferably 50° C. or more, and further more preferably 60° C. or more, from promotion of a smooth reaction. On the other hand, the treatment temperature is more preferably 140° C. or less, and further more preferably 130° C. or less, from the viewpoint of restraint of polymerization or the side reaction.

For a treatment system, a batch system, continuous system, and circuit system are included. The treatment time can be appropriately determined from quantity of (meth)acrylic acid anhydride, a charged amount, or a reaction temperature, however, it is usually 0.5 to 48 hours. The reaction time is preferably 1 hour or more, and more preferably 2 hours or more, from the viewpoint of residual quantity of (meth)acrylic acid anhydride. The reaction time is preferably 36 hours or less, more preferably 24 hours or less, and further more preferably 12 hours or less, from the viewpoint of restraint of polymerization or the side reaction.

In the treatment, a polymerization inhibitor can be used. A kind of a polymerization inhibitor and a using method of it can be applied as well as the kind and the using method of process (1).

The process of the present invention is effective for purification of the (meth)acrylate derived from the alcohol having a phenolic hydroxy group, which is easy to hydrolyze, and especially for purification of phenyl(meth)acrylate that the boiling point is close to the raw materials such as phenol and (meth)acrylic acid.

EXAMPLES

The present invention is described by examples in detail as follows. In embodiments, quantitative analyses are carried out by gas chromatography (a column: DB-5 made in J&B Scientific Corporation, 30 m in length×0.53 mm of an inside diameter and 3 μm of a film thickness; the injection temperature: 200° C.; the detector temperature: 250° C.; and the column temperature and time: holding for 1 minute at 60° C., raising of the temperature with 10° C./min and holding at 250° C.).

Production Example 1

Preparation of Methacryl Acid Anhydride: Practice of Process (1)

A 3-liter, five-necked flask was equipped with a rectification tower (35 mm of an inside diameter, ten steps of theoretical plate), an agitating blade, a thermometer and a air-blowing pipe. To the flask, 918 g (9.0 moles) of acetic anhydride, 1,705 g (19.8 moles) of methacrylic acid, 9.5 g (0.09 moles) of sodium carbonate as the catalyst, and 2.6 g of phenothiazine as the polymerization inhibitor were added. The flask was heated in an oil bath while the internal fluid of the flask was bubbled by air and stirred. After the inner temperature reached to 80° C., the flask was held for 1 hour so that a composition of the solution for reaction reached to equilibrium. In addition, 30 minutes later, reduction of pressure was initiated by starting of a vacuum pump while air bubbling was continued. The reflux condition was set with 70° C. of the solution for reaction and 6.4 kPa of pressure inside of the flask. Then, it was defined as the starting point of the reaction when a distillate was extracted from the top of the tower with reflux ratio 1.5. Eight hours later, a reflux ratio was changed into 2.0 and the reaction was carried out for 24 hours. During this reaction, 96 g of methacrylic acid in which 192 mg of phenothiazine was dissolved was supplied in the top part of the rectification tower for prevention of polymerization in the tower. The temperature of the reaction liquid is slowly raised to 83° C., and a pressure in the flask is slowly lowered to 2.1 kPa. As a result, a distillate containing acetic acid as a main component was extracted from the top of the rectification tower. The distillate was recovered with a cooling pipe cooled at 15° C. and with a trap dipped in liquified nitrogen. After termination of the reaction, the reaction liquid was cooled.

Mass of the reaction liquids at the termination of the reaction is 1,409 g, the composition comprises 75.3% by mass of methacrylic acid anhydride, 0.1% by mass of the mixed acid anhydride, 0% by mass of acetic anhydride, 0% by mass of acetic acid, and 13.1% by mass of methacrylic acid, and the yield of methacrylic acid anhydride was 76.5%. The remains were compounds such as Michael adduct and impurities with high boiling temperature out of detection with a gas chromatograph.

It is noted that yield X (%) of methacrylic acid anhydride is a value calculated with the following formula based on numbers of moles B of anhydrous methacrylic acid in the termination of reaction and numbers of moles A of acetic anhydride added.

$$X = B \div A \times 100$$

There are detected plural peaks to be considered as the compounds that one or two of acetic acid or methacrylic acid were adducted to the double bond of methacrylic acid anhydride by the Michael addition reaction, and the sum of those areas was 9.2% to the total areas.

Example 1

Example of the First Invention (1) Production of the Methacrylate

To a 1-liter, five necked flask with an agitating blade, a thermometer and an air-blowing pipe, 205 g (containing 1.0 mole of methacrylic acid anhydride) of the reaction liquid obtained by the Production example 1 and 104 g (1.1 moles) of phenol were added, and then the reaction was carried out for 5 hours by heating of the flask in an oil bath of 120° C. The compositions of main components of the reaction liquid at the termination of the reaction were shown in Table 1. As other components, there are detected plural peaks to be considered as the compounds (hereinafter referred to as "MA Michael adducts") which are obtained by the Michael addition reaction of acetic acid or methacrylic acid to the double bond of methacrylic acid, and the sum of those areas was 0.8% to the total areas.

(2) Recovery of Methacrylic Acid

A 1-liter flask was equipped with a rectification tower (35 mm of an inside diameter, ten steps of theoretical plate), an agitating blade, a thermometer and an air-blowing pipe. Reduction of pressure was initiated by starting of a vacuum pump while air bubbling was continued. The reflux condition was set with 85° C. of a solution for reaction and 2.4 kPa of pressure inside of the flask. Then, a distillate was extracted from the top of the tower with reflux ratio 1.5. The distillate was recovered with a cooling pipe cooled at 15° C. and with a trap dipped in liquified nitrogen. The pressure inside the flask was lowered to 0.7 kPa to maintain the temperature of the reaction liquid at 83 to 88° C., and the recovery was finished at the point that 125 g of the distillate has been extracted. During this recovery, 24 g of methacrylic acid in which 48 mg of phenothiazine was dissolved was supplied in the top part of the rectification tower for prevention of polymerization in the rectification tower. The compositions of the distillate (recovering-MAA) and the recovery rate of methacrylic acid at this time were shown in Table 1.

It is noted that the ratio of recovery Y (%) of methacrylic acid is a value calculated with the following formula based on numbers of moles D of methacrylic acid in the distillate (recovering-MAA) and numbers of moles C of methacrylic acid in the reaction liquid.

$Y = D \div C \times 100$ (3) Purification of the Methacrylate

A rectification tower was changed to a Vigreux column of 20 cm in length, and simple distillation was carried out. The distillation was carried out by adjusting to 0.2 to 0.6 kPa of a pressure of the vacuum pump side and by raising 75 to 125° C. of the temperature inside the flask. As a result, the first distillate, distillate 2 and distillate 3 were recovered with compositions and quantities shown in Table 2.

Example 2

Example of the Third Invention (1) Production of the Methacrylate

The reaction was carried out in the same manner as in Example 1 except that the temperature of the oil bath was set at 80° C. and the heating time was set for 8 hours. The compositions of main components of the reaction liquid at the termination of the reaction were shown in Table 1. As other components, there are detected plural peaks to be considered as the compounds (hereinafter referred to as "PM Michael adducts") which are obtained by the Michael addition reaction of acetic acid or methacrylic acid to the double bond of phenyl methacrylate and MA Michael adducts, and the sum of those areas was 8.2% to the total areas.

(2) Heat Treatment of the Reaction Product

The temperature of the reaction liquid was raised to 100° C. and heat treatment was carried out for 4 hours because there was much quantity of the Michael adducts. The composition of the reaction liquid after the heat treatment comprised 54.1% by mass of phenyl methacrylate, 38.4% by mass of methacrylic acid, 0.9% by mass of phenol, and 0% by mass of methacrylic acid anhydride. The sum of areas of peaks to be considered as MA Michael adducts as other components was 0.9% to the total areas.

(3) Recovery of Methacrylic Acid

Then, 125 g of a distillate was recovered in the same manner as in Example 1 and the results shown in Table 1 were obtained.

(4) Purification of the Methacrylate

In addition, simple distillation was carried out in the same manner as in Example 1, and the results shown in Table 2 were obtained.

Example 3

Example of the Third Invention

The reaction was carried out in the same manner as in Example 2 except that the temperature of heat treatment of the reaction liquid was changed from 100 to 120° C., and results shown in Table 1 and 2 were obtained.

Example 4

Example of the Second Invention (1) Production of the Methacrylate

The reaction was carried out in the same manner as in Example 2 except that heat treatment of the reaction liquid after termination of the reaction was not carried out. The compositions of main components of the reaction liquid at the termination of the reaction were shown in Table 1. The sum of areas of peaks to be considered as PM Michael adducts and MA Michael adducts as other components was 8.3% to the total areas.

(2) Recovery of Methacrylic Acid

Then, distillation was carried out using the rectification tower in the same manner as in Example 2 except that the pressure and temperature of the reaction liquid in the flask when the distillate was recovered were changed in the following conditions. Namely, in Example 2 (Example 1), the pressure inside the flask was lowered to 0.7 kPa to maintain the temperature of the reaction liquid at 83 to 88° C., and the recovery was finished at the point that 125 g of the distillate has been extracted. On the other hand, in Example 4, the pressure inside the flask was maintained to 2 to 3 kPa to raise the temperature of the reaction liquid to 115° C., and the recovery was finished at the point that 125 g of the distillate has been extracted. The composition of the distillate (recovering-MAA) and recovery rate of methacrylic acid was shown in Table 1.

(3) Purification of the Methacrylate

In addition, simple distillation was carried out in the same manner as in Example 2, and the results shown in Table 2 were obtained.

Example 5

Example of the Fourth Invention (1) Production of the Methacrylate

The methacrylate was produced in the same manner as in Example 2. The compositions of main components of the reaction liquid at the termination of the reaction were shown in Table 1. The sum of areas of peaks to be considered as PM Michael adducts and MA Michael adducts as other components was 8.2% to the total areas.

(2) Recovery of Methacrylic Acid and the Methacrylate

A 1-liter flask was equipped with a Claisen pipe, an agitating blade, a thermometer and an air-blowing pipe, and simple distillation was carried out. The distillation was carried out by adjusting to 0.2 to 0.6 kPa of a pressure of the vacuum pump side and by raising 75 to 125° C. of the temperature inside the flask. There was obtained 274 g of the first distillate containing 44.3% by mass of methacrylic acid, 0.8% by mass of phenol, and 53.2% by mass of phenyl methacrylate.

(3) Recovery of Methacrylic Acid

In the flask with the rectification tower like Example 4, 274 g of the above recovered methacrylate was supplied. Distillation was carried out in the same manner as in Example 4 except that the recovery was finished when 117 g of the distillate has been extracted, and the results shown in Table 1 were obtained.

(4) Purification of the Methacrylate

A rectification tower was changed to a Vigreux column of 20 cm in length, and simple distillation was carried out. The distillation was carried out by adjusting to 0.2 to 0.6 kPa of a pressure of the vacuum pump side and by raising 75 to 125° C. of the temperature inside the flask. The results about the distillate shown in Table 2 were obtained.

Comparative Example 1

(1) Production of the Methacrylate

The oil bath was set at 80° C. and the heating time was set for 8 hours. The reaction was carried out in the same manner as in other conditions of Example 1. The compositions of main components of the reaction liquid at the termination of the reaction were shown in Table 1. The sum of areas of peaks to be considered as PM Michael adducts and MA Michael adducts was 8.3% to the total areas.

(2) Purification of the Methacrylate

A reaction liquid was taken out from the flask, and was dissolved in 1 liter of hexane. Then, the solution was washed once with 1 liter of pure water. One time of washing with 1 liter of 1% by mass of an aqueous sodium hydroxide solution was carried out after one time of washing with 1 liter of 17% by mass of an aqueous sodium carbonate solution. Then, concentration by an evaporator was carried out after two times of washing with 1 liter of pure water. A 1-liter flask was equipped with a Vigreux column of 20 cm in length, an agitating blade, a thermometer and an air-blowing pipe, and simple distillation was carried out after adding of the above concentrated liquid in the flask. The distillation was carried out by adjusting to 0.2 to 0.6 kPa of a pressure of the vacuum pump side and by raising 75 to 125° C. of the temperature inside the flask, and then the results shown in Table 2 were obtained.

It is recognized that quantity of the (meth)acrylate increases, when the reactions were carried out at high temperatures like Example 1 to 4, or when the treatment was at a high temperature. Highly purified (meth)acrylate can be obtained by distillation of this reaction liquid. In addition, (meth)acrylic acid can be recovered in high yield by obtaining of (meth)acrylic acid with decomposition of the Michael adduct.

The content of (meth)acrylic acid increases remarkably and the purity of (meth)acrylic acid decreases in Comparative example 1 in which the reaction is carried out at low temperature and treatment at high temperature, and distillation was not carried out. Therefore, quantity of the (meth)acrylate to be obtained with 99% or more of purity decreases even when purity before the distillation is high. In addition, methacrylic acid can be not recovered by this method.

On the other hand, in Example 5, quantity of the (meth)acrylate and (meth)acrylic acid increase by raising of the distillation temperature at the recovery of (meth)acrylic acid and the (meth)acrylate. Highly purified (meth)acrylate can be obtained by distillation of this recovered liquid.

Example 6

Example of the First and Fifth Invention (1) Production of the Methacrylate and Treatment of Methacrylic Acid Anhydride The methacrylate was produced in the same manner as in Example 1 except that there was used the reaction liquid containing 1.0 mole of methacrylic acid anhydride and 1.0 mole of phenol obtained by the same method as Production example 1. The compositions of main components of the reaction liquid at the termination of the reaction were shown in Table 3. After the reaction, phenol disappeared, and 0.03 moles of methacrylic acid anhydride remained. (Methacrylic acid anhydride remains because a part of phenol reacted with the Michael adduct of methacrylic acid anhydride.)

In this reaction liquid, 0.12 moles of sodium carbonate and 0.24 moles of water are added, and heating was carried out at 80° C. for 2 hours. After the heat treatment, methacrylic acid anhydride disappeared, and 0.001 moles of phenol were detected. The decomposition of phenyl methacrylate was not generated before and after the reaction. The concentration seems to have deteriorated because total mass increased by addition of sodium carbonate and water, however, most of phenyl methacrylate does not decompose.

(2) Recovery of Methacrylic Acid

Methacrylic acid was recovered in the same manner as in Example 1 except that the recovery was finished when 100 g of the distillate has been extracted. The composition of the distillate (recovering-MAA) and recovery rate of methacrylic acid was shown in Table 3.

(3) Purification of the Methacrylate

Distillation was carried out by a method like Example 1. As a result, the first distillate, distillate 2 and distillate 3 were recovered with compositions and quantities shown in Table 4.

Example 7

Example of the Third and Fifth Invention (1) Production of the Methacrylate

The methacrylate was produced in the same manner as in Example 2 except that there was used the reaction liquid obtained by the same method as Production example 1, and there were used 1.0 mole of methacrylic acid anhydride and 1.0 mole of phenol. The compositions of main components of the reaction liquid at the termination of the reaction were shown in Table 3. After the reaction, phenol disappeared, and 0.03 moles of methacrylic acid anhydride remained.

(2) Heat Treatment of the Reaction Product and Treatment of Methacrylic Acid Anhydride Heat treatment was carried out in the same manner as in Example 2 except that 0.26 moles of lithium hydroxide monohydrate were added. The compositions of main components of the reaction liquid after the treatment were shown in Table 3. The concentration does not change because total mass increased by addition of lithium hydroxide monohydrate, however, quantity of phenyl methacrylate increases comparing with one before the heating treatment.

(3) Recovery of Methacrylic Acid

Methacrylic acid was recovered in the same manner as in Example 2 except that the recovery was finished when 100 g of the distillate has been extracted. The compositions of the distillate (recovering-MAA) and recovery rate of methacrylic acid were shown in Table 3.

(4) Purification of the Methacrylate

Distillation was carried out by a method like Example 2. As a result, the first distillate, distillate 2 and distillate 3 were recovered with compositions and quantities shown in Table 4.

Comparative Example 2

(1) Production of the Methacrylate

The reaction liquid obtained by the same method as production example 1, and the oil bath was set at 80° C. and the heating time was set for 8 hours. Then, the reaction was carried out in the same manner as in Example 2 except that 1.1 moles of methacrylic acid anhydride and 1.0 mole of phenol were used. The compositions of main components of the reaction liquid at the termination of the reaction were shown in Table 3. The sum of areas of peaks to be considered as PM Michael adducts and MA Michael adducts was 8.3% to the total areas.

(2) Purification of the Methacrylate

The reaction liquid was taken out from the flask, and was dissolved to 1 liter of hexane. Then, the solution was washed once with 1 liter of pure water. After one time of washing with 1 liter of 17% by mass of aqueous sodium carbonate solution, 0.5 liter of 10% by mass of aqueous sodium hydroxide solution was added and then suspending was carried out at room temperature for 2 hours. The methacrylic acid anhydride disappeared, however, phenyl methacrylate decomposed with 12% by mass. Methacrylic acid and phenol were not detected in a hexane phase because methacrylic acid and phenol generated by hydrolysis dissolved in an aqueous sodium hydroxide solution. The hexane phase was recovered and was washed twice with 1 liter of water. Then, the hexane phase was concentrated with an evaporator. A 1-liter flask was equipped with a Vigreux column of 20 cm in length, an agitating blade, a thermometer and an air-blowing pipe, and simple distillation was carried out after adding of the above concentrated liquid in the flask. The distillation was carried out by adjusting to 0.2 to 0.6 kPa of a pressure of the vacuum pump side and by raising 75 to 125° C. of the temperature inside the flask, and then the results shown in Table 4 were obtained.

As shown in Example 6 and 7, phenol in the reaction liquid can be not contained by use of excessive amount of methacrylic acid anhydride. In addition, methacrylic acid anhydride can be treated without decomposition of phenyl methacrylate. By the method of the present invention, phenyl methacrylate with a little content of phenol can be obtained.

As shown in Comparative example 2, phenol can be removed by alkali-washing, however, phenyl methacrylate decomposes with 10% by mass or more. In addition, methacrylic acid can be not recovered and the liquid containing methacrylic acid is to be disposed as a waste liquid.

Production Example 2

(1) Production of the Methacrylate

The methacrylate was produced in the same manner as in Example 5 except that there was used the reaction liquid obtained by the same method as Production example 1, and there were used 1.1 moles of methacrylic acid anhydride and 1.0 mole of phenol.

(2) Obtaining of a Mixture of Methacrylic Acid and the Methacrylate, Containing Methacrylic Acid Anhydride Distillation was carried out in the same manner as in Example 5, and methacrylic acid and the methacrylate were recovered. There was obtained 250 g of the first distillate containing 42.1% by mass of methacrylic acid, 7.1% by mass of methacrylic acid anhydride, and 50.7% by mass of phenyl methacrylate.

Example 8

Example of the Fifth Invention

To 10.9 g of the mixture (containing 5 mmoles of methacrylic acid anhydride) obtained by Production example 2, 0.21 g (5 mmoles) of lithium hydroxide monohydrate was added. Heat treatment was carried out at 80° C. under agitation for 2 hours.

By heat treatment, methacrylic acid anhydride decomposed with 92% by mass. Decomposition rate of methacrylic acid anhydride after the heat treatment and remaining rate (ratio of the content after the heat treatment to the content before the heat treatment) of phenyl methacrylate are shown in Table 5.

Example 9 to 17

Example of the Fifth Invention

Treatments were carried out in the same manner as in Example 8 except that there were used the compounds and water contents shown in Table 5. Decomposition rate of methacrylic acid anhydride after the heat treatment and remaining rate of phenyl methacrylate are shown in Table 5.

Comparative Example 3 and 4

Treatments were carried out in the same manner as in Example 8 except that water was not used or 10 mmoles of water was used. Decomposition rate of methacrylic acid anhydride after the heat treatment and remaining rate of phenyl methacrylate are shown in Table 5.

Comparative Example 5

Treatments were carried out in the same manner as in Example 8 except that there were used 0.53 g (5 mmoles) of sodium carbonate and 0.48 g (15 mmoles) of methanol.

By the heat treatment, methacrylic acid anhydride decomposed with 99% by mass, however, phenyl methacrylate only remained with 94.4% by mass.

Comparative Example 6

In 10 g of hexane, 10.9 g of the mixture (containing 5 mmoles of methacrylic acid anhydride) obtained by Production example 2 was dissolved. There was added 8 g (10 mmoles) of 5% by mass of an aqueous sodium hydroxide solution, and then suspending was carried out at 40° C. for 1 hour. As a result of analysis of a hexane phase, methacrylic acid anhydride decomposed with 98% by mass, however, phenyl methacrylate only remained with 93.5% by mass.

Comparative Example 7

In 10 g of hexane, 10.9 g of the mixture (containing 5 mmoles of methacrylic acid anhydride) obtained by Production example 2 was dissolved. There was added 21.2 g (20 mmoles) of 10% by mass of an aqueous sodium carbonate solution, and then suspending was carried out at 80° C. for 2 hours. As a result of analysis of a hexane phase, methacrylic acid anhydride decomposed with 2% by mass. Most of phenyl methacrylate did not decompose.

Example 18

Example of the Fifth Invention

The reaction liquid obtained by the same method as Production example 1 was distilled, and methacrylic acid anhydride with 99.9% by mass of purity was obtained. To a 0.1-liter, five-necked flask with an agitating blade, a thermometer, and an air-blowing pipe, there were added 16.3 g (0.105 moles) of methacrylic acid anhydride, 9.4 g (0.1 moles) of phenol, and 1,000 ppm of phenothiazine was added. Then, 0.1 g of concentrated sulfuric acid was titrated in the flask. Reaction was carried out at 80° C. for 5 hours. After the reaction, phenol disappeared, and 0.04 moles of methacrylic acid anhydride remained. To the reaction liquid, 2.5 g (0.06 mmoles) of lithium hydroxide monohydrate was added, and heat treatment was carried out at 80° C. for 2 hours.

By the heat treatment, all of methacrylic acid anhydride decomposed. Phenyl methacrylate decomposed with 0.6% by mass.

TABLE 1

|  | Composition of the reaction liquid at the termination of the reaction (% by mass) | | | | Composition of the reaction liquid after heat treatment (% by mass) | | | Composition of recovering-MAA (% by mass) | | | Recovery rate of MAA |
| --- | --- | --- | --- | --- | --- | --- | --- | --- | --- | --- | --- |
|  | PHMA | MAA | PhOH | MAOMA | PHMA | MAA | PhOH | PHMA | MAA | PhOH | (%) |
| Example 1 | 54.2 | 38.3 | 1.0 | 0 | — | — | — | 0.1 | 99.2 | 0.6 | 87.1 |
| Example 2 | 51.6 | 37.4 | 1.0 | 0 | 54.1 | 38.4 | 0.9 | 0.1 | 99.3 | 0.5 | 87.0 |
| Example 3 | 51.6 | 37.5 | 1.0 | 0 | 54.3 | 38.5 | 0.8 | 0.1 | 99.2 | 0.5 | 86.7 |
| Example 4 | 51.5 | 37.3 | 0.9 | 0 | — | — | — | 0.1 | 99.2 | 0.6 | 86.9 |
| Example 5 | 51.6 | 37.3 | 1.0 | 0 | — | — | — | 0.1 | 99.1 | 0.7 | 83.3 |
| Comparative example 1 | 51.5 | 37.5 | 1.0 | 0 | — | — | — | — | — | — | 0 |

PHMA: Pheny methacrylate,
MAA: Methacrylic acid,
PhOH: Phenol,
MAOMA: methacrylic acid anhydlide

TABLE 2

|  | Composition of the first distillate (% by mass) | | | Recovery amount of the first distillate | Composition of distillate 2 (% by mass) | | | Recovery amount of distillate 2 | Composition of distillate 3 (% by mass) | | | Recovery amount of distillate 3 |
| --- | --- | --- | --- | --- | --- | --- | --- | --- | --- | --- | --- | --- |
|  | PHMA | MAA | PhOH | (g) | PHMA | MAA | PhOH | (g) | PHMA | MAA | PhOH | (g) |
| Example 1 | 49.4 | 45.4 | 5.1 | 42 | 99.6 | 0.2 | 0.2 | 84 | 99.9 | 0.04 | 0.03 | 63 |
| Example 2 | 49.6 | 45.6 | 4.7 | 42 | 99.6 | 0.2 | 0.2 | 64 | 99.9 | 0.03 | 0.04 | 62 |
| Example 3 | 49.7 | 45.7 | 4.5 | 42 | 99.6 | 0.2 | 0.1 | 64 | 99.9 | 0.05 | 0.02 | 62 |

TABLE 2-continued

| | Composition of the first distillate (% by mass) | | | Recovery amount of the first distillate | Composition of distillate 2 (% by mass) | | | Recovery amount of distillate 2 | Composition of distillate 3 (% by mass) | | | Recovery amount of distillate 3 |
|---|---|---|---|---|---|---|---|---|---|---|---|---|
| | PHMA | MAA | PhOH | (g) | PHMA | MAA | PhOH | (g) | PHMA | MAA | PhOH | (g) |
| Example 4 | 49.2 | 45.9 | 4.8 | 42 | 99.6 | 0.2 | 0.2 | 64 | 99.9 | 0.03 | 0.02 | 62 |
| Example 5 | 49.3 | 46.1 | 4.5 | 42 | 99.5 | 0.2 | 0.3 | 64 | 99.8 | 0.1 | 0.1 | 60 |
| Comparative example 1 | 99.7 | 0.1 | 0.1 | 40 | 99.7 | 0.2 | 0.1 | 48 | 98.3 | 1.6 | 0.02 | 63 |

PHMA: Pheny methacrylate,
MAA: Methacrylic acid,
PhOH: Phenol,
MAOMA: methacrylic acid anhydlide

TABLE 3

| | Composition of the reaction liquid at the termination of the reaction (% by mass) | | | | Composition of the reaction liquid after heat treatment (% by mass) | | | | Composition of recovering-MAA (% by mass) | | | Recovery rate of MAA |
|---|---|---|---|---|---|---|---|---|---|---|---|---|
| | PHMA | MAA | PhOH | MAOMA | PHMA | MAA | MAOMA | PhOH | PHMA | MAA | PhOH | (%) |
| Example 6 | 52.7 | 35.1 | 0 | 1.3 | 49.9 | 30.8 | 0.0 | 0.03 | 0.1 | 99.7 | 0.1 | 82.1 |
| Example 7 | 51.2 | 34.7 | 0 | 1.4 | 51.0 | 31.1 | 0.0 | 0.03 | 0.1 | 99.6 | 0.1 | 82.9 |
| Comparative example 2 | 51.3 | 34.8 | 0 | 1.3 | — | — | — | — | — | — | — | 0 |

PHMA: Pheny methacrylate,
MAA: Methacrylic acid,
PhOH: Phenol,
MAOMA: methacrylic acid anhydlide

TABLE 4

| | Composition of the first distillate (% by mass) | | | Recovery amount of the first distillate | Composition of distillate 2 (% by mass) | | | Recovery amount of distillate 2 | Composition of distillate 3 (% by mass) | | | Recovery amount of distillate 3 |
|---|---|---|---|---|---|---|---|---|---|---|---|---|
| | PHMA | MAA | PhOH | (g) | PHMA | MAA | PhOH | (g) | PHMA | MAA | PhOH | (g) |
| Example 6 | 54.7 | 45.2 | 0 | 42 | 99.8 | 0.2 | 0 | 62 | 99.9 | 0.05 | 0 | 60 |
| Example 7 | 54.5 | 45.4 | 0 | 42 | 99.8 | 0.2 | 0 | 62 | 99.9 | 0.05 | 0 | 60 |
| Comparative example 2 | 99.6 | Trace amount | 0.1 | 42 | 99.9 | 0.1 | 0 | 48 | 99.9 | 0.04 | 0 | 30 |

PHMA: Pheny methacrylate,
MAA Methacrylic acid,
PhOH: Phenol,
MAOMA methacrylic acid anhydlide

TABLE 5

| | Compound | Amount (mmol) | Amount of water (mmol) | Decomposition rate of MAOMA (%) | Remaining rate of PHMA (%) |
|---|---|---|---|---|---|
| Example 8 | Lithium hydrooxide monohydrate | 5 | 0 | 92 | 99.4 |
| Example 9 | Lithium hydrooxide monohydrate | 10 | 0 | 100 | 99.0 |
| Example 10 | Lithium hydrooxide monohydrate | 5 | 10 | 100 | 99.2 |
| Example 11 | Lithium carbonate | 10 | 5 | 100 | 99.2 |
| Example 12 | Sodium hydroxide | 10 | 0 | 100 | 98.2 |
| Example 13 | Sodium carbonate | 5 | 0 | 93 | 99.5 |
| Example 14 | Sodium carbonate | 5 | 5 | 99 | 99.0 |

TABLE 5-continued

| | Compound | Amount (mmol) | Amount of water (mmol) | Decomposition rate of MAOMA (%) | Remaining rate of PHMA (%) |
|---|---|---|---|---|---|
| Example 15 | Potassium carbonate | 5 | 10 | 100 | 98.6 |
| Example 16 | Magnesium hydroxide | 10 | 0 | 100 | 98.5 |
| Example 17 | Calcium hydroxide | 10 | 0 | 100 | 98.4 |
| Comparative example 3 | none | 0 | 0 | 1 | 99.9 |
| Comparative example 4 | none | 0 | 10 | 5 | 99.9 |

The invention claimed is:

1. A method for producing a (meth)acrylate, the method comprising:
   (1) producing (meth)acrylic acid anhydride, comprising reacting a fatty acid anhydride of formula (I)

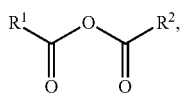

wherein
   $R^1$ is a linear or branched, alkyl group or alkenyl group, having a carbon number 1 to 3, and
   $R^2$ is a linear or branched alkyl group having a carbon number 1 to 3,
   with (meth)acrylic acid to produce (meth)acrylic acid anhydride, while extracting a fatty acid produced as a by-product;
   (2) obtaining the (meth)acrylate by reacting a phenol with crude (meth)acrylic acid anhydride obtained by the producing (1), wherein the obtaining (2) is carried out at a temperature in a range of 90° C. or more and 120° C. or less; and
   (3) recovering (meth)acrylic acid by distillation.

2. A method for producing a (meth)acrylate, the method comprising:
   (1) producing (meth)acrylic acid anhydride, comprising reacting a fatty acid anhydride of formula (I)

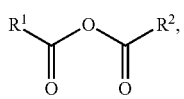

wherein
   $R^1$ is a linear or branched, alkyl group or alkenyl group, having a carbon number 1 to 3, and
   $R^2$ is a linear or branched alkyl group having a carbon number 1 to 3,
   with (meth)acrylic acid to produce (meth)acrylic acid anhydride, while extracting a fatty acid produced as a by-product;
   (2) obtaining the (meth)acrylate by reacting a phenol with crude (meth)acrylic acid anhydride obtained by the producing (1); and
   (3) recovering (meth)acrylic acid by distillation at a temperature in a range of 90° C. or more and 130° C. or less.

3. A method for producing a (meth)acrylate, the method comprising:
   (1) producing (meth)acrylic acid anhydride, comprising reacting a fatty acid anhydride of formula (I)

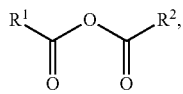

wherein
   $R^1$ is a linear or branched, alkyl group or alkenyl group, having a carbon number 1 to 3, and
   $R^2$ is a linear or branched alkyl group having a carbon number 1 to 3,
   with (meth)acrylic acid to produce (meth)acrylic acid anhydride, while extracting a fatty acid produced as a by-product;
   (2) obtaining the (meth)acrylate by reacting a phenol with crude (meth)acrylic acid anhydride obtained by the producing (1);
   (2') heating the reaction liquid obtained by the obtaining (2) at a temperature in the range of 90° C. or more and 130° C. or less; and
   (3) recovering (meth)acrylic acid by distillation.

4. A method for producing a (meth)acrylate, the method comprising:
   (1) producing (meth)acrylic acid anhydride, comprising reacting a fatty acid anhydride of formula (I)

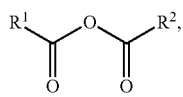

wherein
   $R^1$ is a linear or branched, alkyl group or alkenyl group, having a carbon number 1 to 3, and
   $R^2$ is a linear or branched alkyl group having a carbon number 1 to 3,
   with (meth)acrylic acid to produce (meth)acrylic acid anhydride, while extracting a fatty acid produced as a by-product;
   (2) obtaining the (meth)acrylate by reacting a phenol with crude (meth)acrylic acid anhydride obtained by the producing (1);
   (2") obtaining a reaction liquid containing (meth)acrylic acid and the (meth)acrylate by distillation of the reaction liquid obtained by the obtaining (2) at a temperature in a range of 90° C. or more and 130° C. or less; and
   (3) recovering (meth)acrylic acid by distillation.

5. The method of claim 1, wherein the (meth)acrylic acid anhydride remaining in a reaction liquid obtained by the obtaining (2) is hydrolyzed by addition of at least one basic compound selected from the group consisting of a hydroxide, a carbonate, a bicarbonate, and an oxide of at least one selected from the group consisting of an alkali metal and an alkaline earth metal to a reaction liquid obtained by the obtaining (2).

6. The method of claim 2, wherein the (meth)acrylic acid anhydride remaining in a reaction liquid obtained by the obtaining (2) is hydrolyzed by addition of at least one basic compound selected from the group consisting of a hydroxide, a carbonate, a bicarbonate, and an oxide of at least one selected from the group consisting of an alkali metal and an alkaline earth metal to the reaction liquid obtained by the obtaining (2).

7. The method of claim 3, wherein the (meth)acrylic acid anhydride remaining in a reaction liquid obtained by the obtaining (2) is hydrolyzed by addition of at least one basic compound selected from the group consisting of a hydroxide, a carbonate, a bicarbonate, and an oxide of at least one selected from the group consisting of an alkali metal and an alkaline earth metal to the reaction liquid obtained by the obtaining (2).

8. The method of claim 4, wherein the (meth)acrylic acid anhydride remaining in a reaction liquid obtained by the obtaining (2) is hydrolyzed by addition of at least one basic compound selected from the group consisting of a hydroxide, a carbonate, a bicarbonate, and an oxide of at least one selected from the group consisting of an alkali metal and an alkaline earth metal to the reaction liquid obtained by the obtaining (2).

9. The method of claim 5, wherein the (meth)acrylic acid anhydride is hydrolyzed by addition of 0.1 to 10 moles of water for 1 mole of the (meth)acrylic acid anhydride remaining in the reaction liquid obtained by the obtaining (2), to the reaction liquid.

10. The method of claim 6, wherein the (meth)acrylic acid anhydride is hydrolyzed by addition of 0.1 to 10 moles of water for 1 mole of the (meth)acrylic acid anhydride remaining in the reaction liquid obtained by the obtaining (2), to the reaction liquid.

11. The method of claim 7, wherein the (meth)acrylic acid anhydride is hydrolyzed by addition of 0.1 to 10 moles of water for 1 mole of the (meth)acrylic acid anhydride remaining in the reaction liquid obtained by the obtaining (2), to the reaction liquid.

12. The method of claim 8, wherein the (meth)acrylic acid anhydride is hydrolyzed by addition of 0.1 to 10 moles of water for 1 mole of the (meth)acrylic acid anhydride remaining in the reaction liquid obtained by the obtaining (2), to the reaction liquid.

13. The method of claim 1, wherein, in the fatty acid anhydride of formula (I), $R^1$ is a linear alkyl group.

14. The method of claim 1, wherein, in the fatty acid anhydride of formula (I), $R^1$ is a branched alkyl group.

15. The method of claim 1, wherein, in the fatty acid anhydride of formula (I), $R^1$ has a carbon number 1.

16. The method of claim 1, wherein, in the fatty acid anhydride of formula (I), $R^1$ has a carbon number 2.

17. The method of claim 1, wherein, in the fatty acid anhydride of formula (I), $R^1$ has a carbon number 3.

18. The method of claim 13, wherein, in the fatty acid anhydride of formula (I), $R^1$ has a carbon number 3.

* * * * *